(12) United States Patent
Campbell

(10) Patent No.: US 11,857,309 B2
(45) Date of Patent: Jan. 2, 2024

(54) RESPIRATION MONITORING DEVICE AND METHODS FOR USE

(71) Applicant: Casey Marie Campbell, Sinton, TX (US)

(72) Inventor: Casey Marie Campbell, Sinton, TX (US)

(*) Notice: Subject to any disclaimer, the term of this patent is extended or adjusted under 35 U.S.C. 154(b) by 212 days.

(21) Appl. No.: 16/784,622

(22) Filed: Feb. 7, 2020

(65) Prior Publication Data
US 2020/0253508 A1    Aug. 13, 2020

Related U.S. Application Data

(60) Provisional application No. 62/802,420, filed on Feb. 7, 2019.

(51) Int. Cl.
*A61B 5/08*    (2006.01)
*A61B 7/00*    (2006.01)
*A61B 5/00*    (2006.01)
*A61B 5/113*   (2006.01)

(52) U.S. Cl.
CPC .......... *A61B 5/0816* (2013.01); *A61B 5/1135* (2013.01); *A61B 5/7275* (2013.01); *A61B 7/003* (2013.01); *A61B 5/7246* (2013.01); *A61B 5/746* (2013.01); *A61B 2562/0204* (2013.01); *A61B 2562/0219* (2013.01)

(58) Field of Classification Search
CPC .......... A61B 5/0816; A61B 2562/0204; A61B 2562/0219; A61B 5/1135; A61B 5/7246; A61B 5/7242; A61B 5/7239; A61B 5/725; A61B 7/003; A61B 5/087; A61B 5/113; A61B 5/6823; A61B 5/742
USPC ................................................ 600/534, 595
See application file for complete search history.

(56) References Cited

U.S. PATENT DOCUMENTS

| 4,305,400 | A |    | 12/1981 | Logan |
|---|---|---|---|---|
| 6,522,266 | B1 | * | 2/2003 | Soehren .............. G01C 21/16 |
|   |   |   |   | 600/595 |
| 8,690,799 | B2 |   | 4/2014 | Telfort et al. |
| 9,610,042 | B1 | * | 4/2017 | Vyshedskiy .......... A61B 5/01 |
| 9,826,940 | B1 | * | 11/2017 | Lengerich .......... A61B 5/721 |

(Continued)

FOREIGN PATENT DOCUMENTS

WO    WO-2007088539 A2 *  8/2007  .......... A61B 5/0205

*Primary Examiner* — Jacqueline Cheng
*Assistant Examiner* — Jonathan E. Cooper
(74) *Attorney, Agent, or Firm* — Edmonds & Cmaidalka, P.C.

(57) ABSTRACT

Embodiments of the present disclosure provide respiration monitoring systems and methods for using same. The respiration monitoring device can include a first accelerometer, a second accelerometer, at least one acoustic sensor, a memory comprising a lookup table, a real-time clock, and one or more instructions, and a processor for receiving one or more motion signals from each accelerometer and one or more sound signals from each acoustic sensor. The processor can correlate the one or more motion signals to a distance value, correlate the one or more sound signals to a sound value, filter the distance value and the sound value according to limitations stored in the lookup table, assign a time stamp to each filtered value, determine local maximums for the filtered motion values and local minimums for the filtered sound values, and match the local maximums to the local minimums to confirm a completed breath.

19 Claims, 4 Drawing Sheets

(56) References Cited

U.S. PATENT DOCUMENTS

| | | | |
|---|---|---|---|
| 2007/0112287 A1* | 5/2007 | Fancourt | A61B 5/6838 600/595 |
| 2011/0092780 A1* | 4/2011 | Zhang | A61B 5/053 600/301 |
| 2011/0190651 A1* | 8/2011 | Ota | A61B 7/003 600/534 |
| 2011/0218458 A1* | 9/2011 | Valin | A61B 34/20 600/595 |
| 2014/0275836 A1* | 9/2014 | Chang | A61M 16/0411 600/301 |
| 2015/0313484 A1* | 11/2015 | Burg | A61B 5/021 600/301 |
| 2016/0270718 A1* | 9/2016 | Heneghan | A61B 7/003 |
| 2017/0055896 A1* | 3/2017 | Al-Ali | A61B 5/1116 |
| 2017/0172459 A1* | 6/2017 | Bernstein | A61B 5/0816 |
| 2018/0000426 A1* | 1/2018 | Li | A61B 5/742 |
| 2021/0113114 A1* | 4/2021 | Murgas | A61B 5/7278 |

* cited by examiner

RESPIRATION MONITORING DEVICE AND METHODS FOR USE

CROSS-REFERENCE TO RELATED APPLICATIONS

This application claims priority to U.S. Provisional patent application having Ser. No. 62/802,420, filed on Feb. 7, 2019. The entirety of which is incorporated by reference herein.

BACKGROUND

Field of the Invention

Embodiments of the present disclosure generally relate to monitoring and recording health and wellness. More particularly, embodiments of the present disclosure relate to respiration monitoring devices and uses thereof.

Description of the Related Art

Diagnostics play a critical role in monitoring and assessing the health of patients. To better serve the needs of patients, medical experts routinely take measurements and record patient histories. Such measurements are typically acquired through medical telemetry techniques that require a diverse variety of technologies and devices to gather, record, and transmit the data. Patient care and comfort must also be considered when gathering this data due to the invasive or encumbering nature of typical telemetric devices.

Conventional respiration monitoring systems require direct contact to a patient's skin around the torso or neck areas. Other conventional respiration monitoring systems require direct contact with the air passing through the airway of a patient, such as with a mask or nasal canula. Some conventional respiration monitoring systems are only used for permanent monitoring and are not designed for intermittent use. Other conventional respiration monitoring systems only transmit data to external monitors or computer systems and provide no monitor display on the system itself.

There is a need, therefore, for a respiration monitoring device that does not require direct contact with a patient's skin, is capable of monitoring respiration for any length of time, is capable of transmitting data to external devices, and has a display monitor.

SUMMARY

Embodiments of the present disclosure provide respiration monitoring systems and methods for using same. The respiration monitoring device can include a first accelerometer for detecting a motion in the x, y and z-axis, a second accelerometer for detecting a rotation about the z-axis, at least one acoustic sensor for detecting sound related to the patient's breath, a memory comprising a lookup table, a real-time clock, and one or more instructions, and a processor for receiving one or more motion signals from each accelerometer and one or more sound signals from each acoustic sensor. The processor can correlate the one or more motion signals to a distance value, correlate the one or more sound signals to a sound value, filter the distance value and the sound value according to limitations stored in the lookup table, assign a time stamp to each filtered value using the real-time clock within the memory, determine local maximums for the filtered motion values and local minimums for the filtered sound values, and match the local maximums for the filtered motion values to the local minimums for the filtered sound values to confirm a completed breath from the patient.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is emphasized that the figures are not necessarily to scale and certain features and certain views of the figures can be shown exaggerated in scale or in schematic for clarity and/or conciseness.

DETAILED DESCRIPTION

Figure 1:
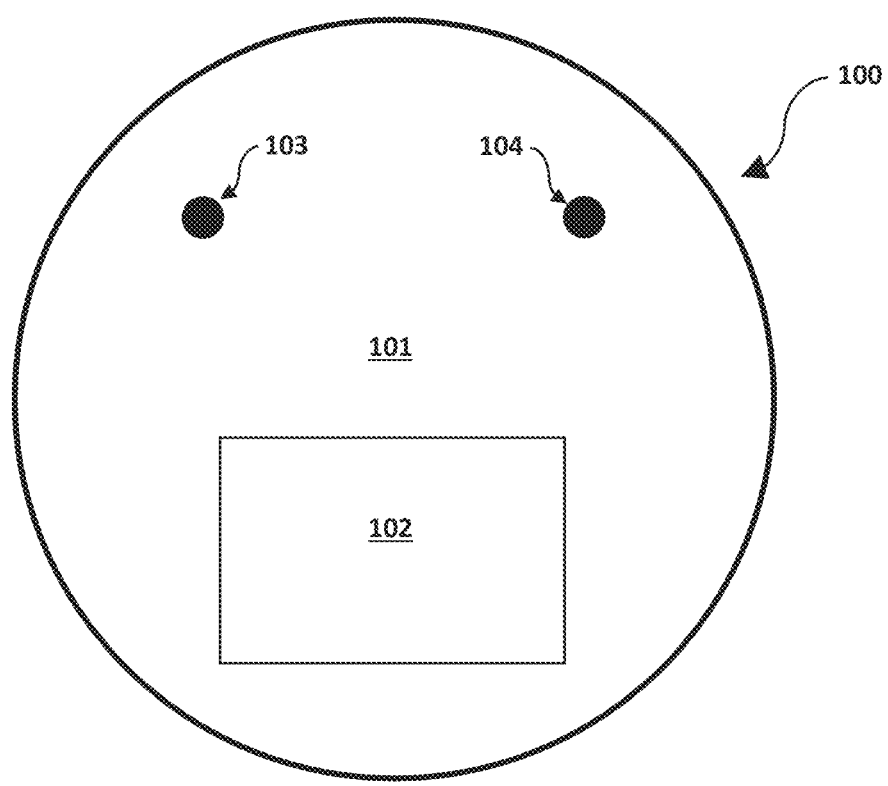
FIG. 1 depicts a schematic of an exterior of an illustrative respiration monitoring device, according to one or more embodiments described.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various embodiments and across the figures provided herein. This repetition is for the purpose of simplicity and clarity and does not in itself dictate a relationship between the various embodiments and/or configurations. Moreover, the formation of a first feature over or on a second feature in the description that follows can include embodiments in which the first and second features are formed in direct contact, and can also include embodiments in which additional features can be formed interposing the first and second features, such that the first and second features are not in direct contact. Finally, the embodiments presented below can be combined in any combination of ways, i.e., any element from one embodiment can be used in any other embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function. Additionally, in the following discussion and in the claims, the terms "including" and "comprising" are used in an open-ended fashion, and thus should be interpreted to mean "including, but not limited to."

All numerical values in this disclosure can be exact or approximate values unless otherwise specifically stated. Accordingly, various embodiments of the disclosure can deviate from the numbers, values, and ranges disclosed herein without departing from the intended scope. Furthermore, the term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise.

The terms "up" and "down"; "upward" and "downward"; "upper" and "lower"; "upwardly" and "downwardly"; "above" and "below"; and other like terms as used herein refer to relative positions to one another and are not intended to denote a particular spatial orientation since the apparatus and methods of using the same can be equally effective at various angles or orientations.

A detailed description of the respiration monitoring device and methods for using the same will now be provided. Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

FIG. 1 depicts a schematic of an exterior of an illustrative respiration monitoring device 100, according to one or more embodiments. The respiration monitoring device 100 can include a case or enclosure 101 that provides a housing for a display screen 102, power button 103, and/or reset button 104. The case 101 can include an adhesive, clip or other mechanism for attaching the device 100 to a patient to be monitored. Exemplary locations include direct contact to the patient's body (e.g., skin, hair, fur, scales, feathers, or the like) or indirect contact via clothing (e.g., shirts, undershirts, gowns, blouses, or the like), badges, necklaces, wrappings, or the like, on or near the torso of the patient. For example, the case 101 can best attach to the breast pocket of a shirt. The term "patient" as used herein refers to humans as well as any other breathing life form, including dogs, cats, cows, sheep, pigs, reptiles, fish, whales, sharks, and all other animals. The case 101 can be readily detached from the patient after the monitoring period ends. The respiration monitoring device 100 can be made of any one or more disposable materials or sterilizable materials (e.g., plastics, stainless steel, glass, rubber, or the like) for reuse. The respiration monitoring device 100 can be disposable and intended for a single use or for a single patient and then be thrown away. The respiration monitoring device 100 can also be sterilized after each use or after each patient. The respiration monitoring device 100 can re-used multiple times for the same patient or for multiple patients or for single use only.

The power button 103 can initiate a monitoring process and the reset button 104 can restart an ongoing monitoring process. The monitoring process can be performed automatically by the respiration monitoring device 100. The respiration monitoring device 100 can perform the monitoring process hands-free from any operator (e.g. holding the device, manual counting, manual timing, manual calculations, or the like). Hands-free operation has a distinct advantage over manual operation because it can minimize the opportunity for operator error.

The display screen 102 can display the rate of respiration. The monitoring display 102 can also be used to display the date, time, unit ID, and/or battery status of the device 100. The size of the display screen 102 can vary and is typically as big as the case 101 will allow.

The respiration monitoring device 100 can also include RF, IR, WiFi, cellular, or other suitable modes of communication for transmitting output information to a receiver or other device that is located remotely from the patient, such as a nurse's station or call center or the like.

Figure 2:
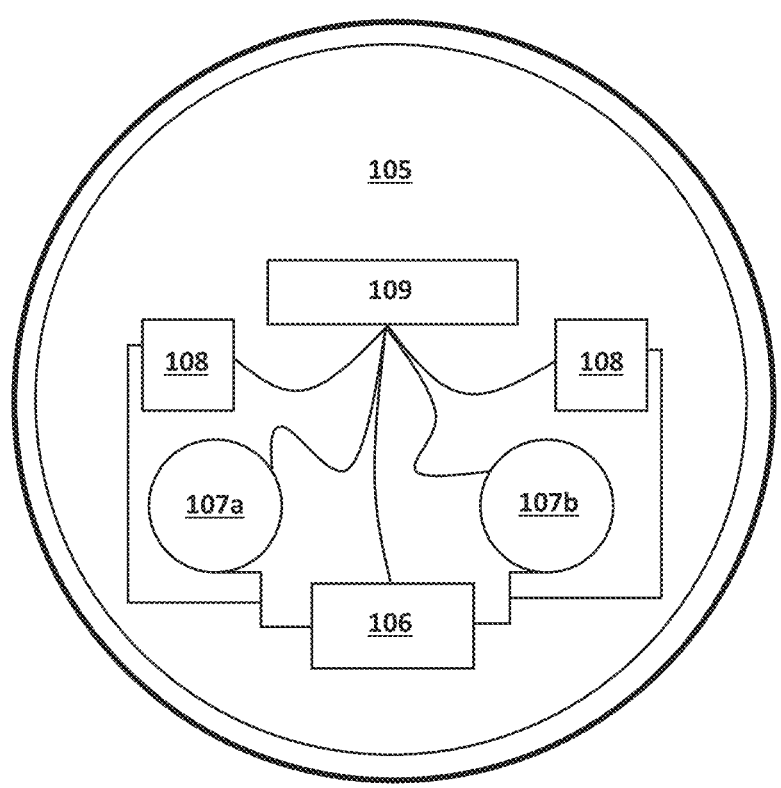
FIG. 2 depicts a schematic of an interior of the illustrative respiration monitoring device, according to one or more embodiments described.

FIG. 2 depicts a schematic of an interior of the respiration monitoring device 100, according to one or more embodiments. The interior case 105 can include a controller 106, two or more accelerometers 107A,B, at least one acoustic sensor 108, and a power supply 109.

The accelerometers 107A,B can be any suitable motion detection device capable of detecting motion in the x-, y-, and z-axis direction, and/or rotation relative to the z-axis (i.e. "tilt"). As used herein, the "x-axis" refers to the axis that goes side to side in a horizontal plane, the "y-axis" refers to the axis that is up to down in a vertical plane and is orthogonal to the x-axis, and the "z-axis" is forward to backward in the same horizontal plane as the x-axis.

Each accelerometer 107A,B can contain a cantilever beam attached to a mass and a fixed beam. Under the influence of external accelerations, i.e. the patient's breath, the mass deflects from its neutral position and this deflection can be measured in an analog or digital manner. The accelerometers 107A,B can measure deflection by measuring capacitance between a set of fixed beams and a set of beams attached to the mass. The measured acceleration can be output to other devices from the accelerometers 107A,B as a motion signal containing analog or digital data.

In operation, the device 100 is placed on the patient, preferably near or proximate the heart or lungs. The first or motion accelerometer 107A within the device 100 measures or otherwise determines the x-, y-, and z-axis accelerations based on relative displacement of the device 100, which is caused by the patient's breathing. The second or rotation accelerometer 107B within the device 100 measures or otherwise determines the rotation of the device 100 relative to the z-axis (i.e. "tilt"), which may also be caused by the patient's breathing. As used herein, the term "tilt" refers to rotation relative to the z-axis. Suitable accelerometers 107A,B are capable of detecting accelerations greater than 40 cm/sec$^2$, greater than 60 cm/sec$^2$, and greater than 80 cm/sec$^2$. For example, suitable accelerometers 107A,B can detect accelerations of about 40 cm/sec$^2$, about 60 cm/sec$^2$, or about 80 cm/sec$^2$ to about 120 cm/sec$^2$, about 180 cm/sec$^2$, or about 240 cm/sec$^2$.

The acoustic sensor 108 can be any sensor that is capable of detecting sound between 0 Hz and 1500 Hz. The acoustic sensor 108 can contain a flexible membrane and a fixed plate with perforations. Under the influence of external sound waves, the flexible membrane deflects due to changes in pressure, and this deflection can be measured in an analog or digital manner. In a preferred embodiment, two or more acoustic sensors 108 are used. Any two acoustic sensors 108 can be spaced apart to provide stereophonic data. For example, the sensors 108 can be spaced 1 mm to 5 mm apart, 5 mm to 20 mm apart, or 20 mm to 75 mm apart. Stereophonic data is sound data produced by a pair of acoustic sensors in which specific sounds can be located and isolated through triangulation. Monophonic data is sound data produced by a single acoustic sensor. Stereophonic data has a distinct advantage over monophonic data because it provides more accurate sound detection. The measured sound can be output to other devices from the acoustic sensor 108 as a sound signal containing analog or digital data.

Figure 3:
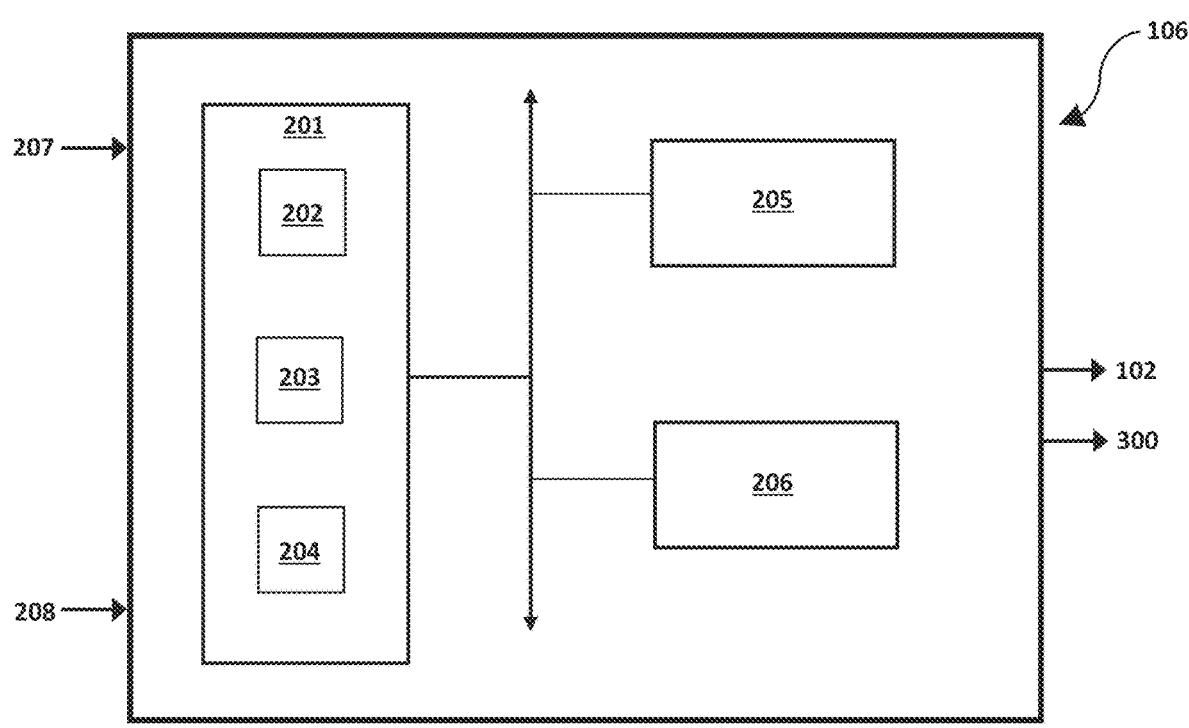
FIG. 3 depicts a schematic of an illustrative respiration monitoring device processor, according to one or more embodiments described.

FIG. 3 depicts a schematic of an illustrative respiration monitoring device controller 106, according to one or more embodiments. The controller 106 can include a memory 201, a processor 205, and a network adapter 206. The controller 106 can receive a motion signal from the accelerometers 107A,B which provide respiratory motion data 207 and a sound signal from the acoustic sensors 108 which provide respiratory sound data 208. The controller 106 can provide output to the display screen 102 or one or more external devices 300.

The memory 201 can store respiratory motion data 207 and respiratory sound data 208. The memory 201 can include one or more lookup tables 202 containing distance values and/or sound values, a real-time clock 203, and processor instructions 204. The processor instructions 204 direct the processor 205 to filter respiratory motion data 207 using the lookup table 202 in order to remove motion (e.g., standing, sitting, sitting up, laying down, talking, or the like) that is not associated with breathing. The processor instructions 204 can contain an algorithm to convert accelerations detected by the accelerometers 107A,B to distance values using time data from the real-time clock 203. The processor instructions 204 can contain a filter to remove distance values greater than 5 cm, greater than 7.5 cm, and greater than 10 cm. The processor instructions 204 can further direct the processor 205 to calculate local maximum distance values in order to determine when the patient is between inhalation and exhalation based upon the accelerometers 107A,B. The processor instructions 204 can direct the processor 205 to filter respiratory sound data 208 using the lookup table 202 in order to remove sound values (e.g., heartbeat, intestinal, stomach, talking, coughing, sneezing, standing, sitting, or the like) that are not associated with breathing. The processor instructions 204 can contain a filter to remove sound values lesser than 600 Hz, lesser than 500 Hz, and lesser than 400 Hz, and greater than 1100 Hz, greater than 1200 Hz, and greater than 1300 Hz. The processor instructions 204 can further direct the processor 205 to calculate local minimum sound values in order to determine when the patient is between inhalation and exhalation based upon the acoustic sensors 108. The processor instructions 204 can then direct the processor 205 to count and store a completed breath by comparing the time of local maximum distance value and the time of local minimum sound value. Local minimum respiratory sound data can occur between every inhalation and exhalation. Local maximum distance values can only occur after inhalation and before exhalation. The processor 205 can count completed breaths by counting every local maximum distance value that occurs during a local minimum sound value. The processor 205 can then calculate a respiration rate by dividing breath count by time elapsed according to the real-time clock 203. In a preferred embodiment, the processor 205 can send the respiration rate to the display screen 102.

In some cases it can be necessary to account for input disruptions in the respiratory motion data 207 or respiratory sound data 208. In such cases, the recording process can be reset using the reset button 104. The processor 205 cannot count completed breaths without comparing the times of distance values and sound values. Exemplary input disruptions include nearby conversation, environmental noises, sudden movement, repositioning of the respiration monitoring device, or the like.

The network adapter 206 can receive the calculated respiration rate from the processor 205. The network adapter 206 can transmit data from the respiration monitoring device 100 to an external device 300. In one example, the network adapter 206 transmits data to an external computer system wirelessly.

Figure 4:
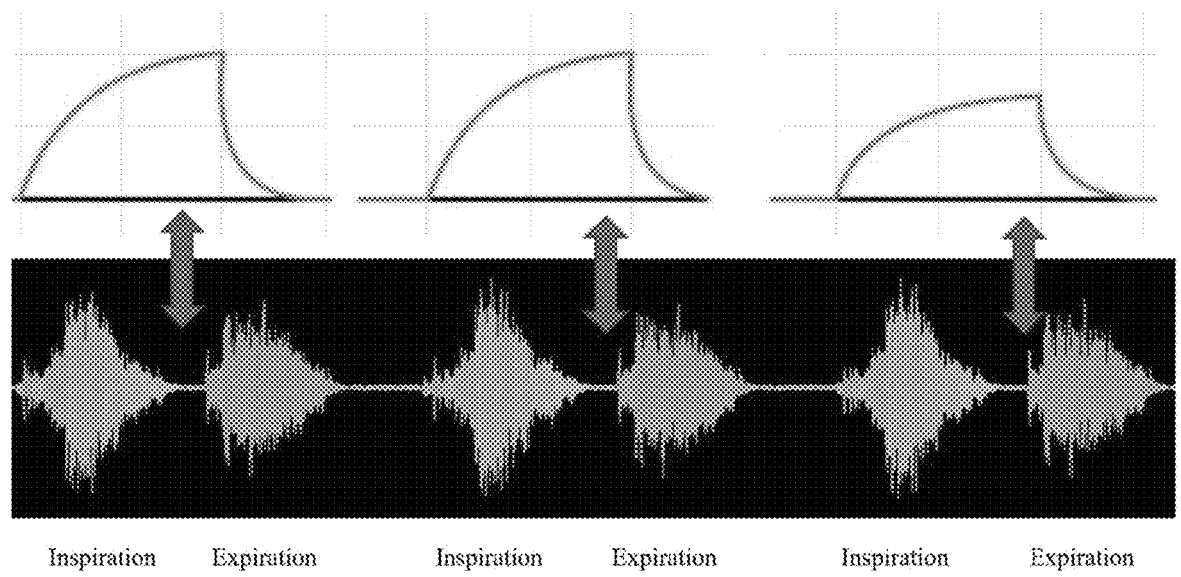
FIG. 4 depicts a graph illustrating a relationship between respiration sounds and respiration motion, according to one or more embodiments described.

FIG. 4 depicts a graph illustrating a relationship between respiration sounds and respiration motion, according to one or more embodiments. The graph illustrates the filtered distance values and filtered sound values from the processor 205. The actual distance values and sound values during operation can be different than shown.

Embodiments of the present disclosure further relate to any one or more of the following paragraphs:

1. A device for determining respirations in a patient, the device comprising a first accelerometer for detecting a motion in the x, y and z-axis; a second accelerometer for detecting a rotation about the z-axis; at least one acoustic sensor for detecting sound related to the patient's breath; a memory comprising a lookup table, a real-time clock, and one or more instructions; a processor for receiving one or more motion signals from each accelerometer and one or more sound signals from each acoustic sensor, wherein the processor: receives the one or more signals from each accelerometer and correlates the one or more signals to a distance value; receives the one or more signals from the acoustic sensors and correlates the one or more signals to a sound value; filters the distance value and the sound value according to limitations stored in the lookup table; assigns a time stamp to each filtered value using the real-time clock within the memory; determines local maximums for the filtered motion values and local minimums for the filtered sound values; and matches the local maximums for the filtered motion values to the local minimums for the filtered sound values to confirm a completed breath from the patient.

2. The device of paragraph 1, wherein the memory further comprises instructions that cause the processor to disregard the local minimums for the filtered sound values that do not match the local maximums for the filtered motion values.

3. The device of paragraph 1 or 2, wherein the memory further comprises instructions that cause the processor to count the completed breaths and calculate a respiration rate using the real-time clock within the memory.

4. The device according to any paragraph 1 to 3, further comprising a display screen configured to display the respiration rate.

5. The according to any paragraph 1 to 4, wherein the memory further comprises instructions that cause the processor to wirelessly transfer the complete breath count to an external device.

6. The according to any paragraph 1 to 5, wherein the device is attachable to a surface on the body.

7. The according to any paragraph 1 to 6, wherein the device is made of disposable materials.

8. A method for monitoring respirations in a patient, comprising: disposing a device on a surface of the body wherein the device comprises: locating a device about a surface of the patient, wherein the device comprises: a first accelerometer for detecting a motion in the x, y and z-axis; a second accelerometer for detecting a rotation about the z-axis; at least one acoustic sensor for detecting sound related to the patient's breath; a memory comprising a lookup table, a real-time clock, and one or more instructions; and a processor for receiving one or more signals from each accelerometer, the one or more signals correlate to a distance value for the motion detected by the accelerometers; receives one or more signals from the acoustic sensors, wherein the one or more signals correlate to a sound value for the sound detected by the acoustic sensors; filters the distance value and sound value according to limitations stored in the lookup table; assigns a time stamp to each filtered value using the real-time clock within the memory; determines local maximums for the filtered motion values and local minimums for the filtered sound values; and matches the local maximums for the filtered motion values to the local minimums for the filtered sound values to confirm a completed breath from the patient.

9. The method according to paragraph 8, wherein the memory further comprises instructions that cause the processor to disregard the local minimums for the filtered sound values that do not match the local maximums for the filtered motion values.

10. The method according to paragraph 8 or 9, wherein the memory further comprises instructions that cause the processor to count the completed breaths and calculate a respiration rate using the real-time clock within the memory.

11. The method according to any paragraph 8 to 10, wherein the device further comprises a display screen, wherein the display screen displays the respiration rate.

12. The method according to any paragraph 8 to 11, wherein the memory further comprises instructions that cause the processor to wirelessly transfer the counted breath count to an external device.

13. The method according to any paragraph 8 to 12, wherein the device is attachable to a surface on the body.

14. The method according to any paragraph 8 to 13, wherein the device is disposable after a single use or a single patient.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A device for determining respiration in a patient, the device comprising:
    a first accelerometer for detecting a motion in the x, y and z-axis;
    a second accelerometer for detecting a tilt about the z-axis;
    at least one acoustic sensor for detecting sound related to the patient's breath;
    a memory comprising a lookup table, a real-time clock, and one or more instructions;
    a processor configured to:
        calculate motion values from signals received from the first accelerometer;
        calculate tilt values from signals received from the second accelerometer;
        calculate sound values from signals received from the acoustic sensor;
        filters the motion values and the tilt values according to limitations stored in the lookup table, to provide filtered motion values;
        filters the sound values according to limitations stored in the lookup table, to provide filtered sound values;
        assigns a time stamp to each filtered motion value and each filtered sound value using the real-time clock within the memory;
        determines local maximums for the filtered motion values and local minimums for the filtered sound values; and
        counts and stores a completed breath for every time one of the local maximums for the filtered motion values occurs during one of the local minimums for the filtered sound values.

2. The device of claim 1, wherein the memory further comprises instructions that cause the processor to disregard the local minimums for the filtered sound values that do not match the local maximums for the filtered motion values.

3. The device of claim 1, wherein the memory further comprises instructions that cause the processor to count the completed breaths and calculate a respiration rate using the assigned time stamps.

4. The device of claim 3, further comprising a display screen configured to display the respiration rate.

5. The device of claim 3, wherein the memory further comprises instructions that cause the processor to wirelessly transfer the complete breath count to an external device.

6. The device of claim 1, wherein the device is attachable to a surface on the body.

7. The device of claim 1, wherein the device is disposable.

8. A method for monitoring respiration in a patient, comprising:
locating a device about a surface of the patient, wherein the device comprises:
a first accelerometer for detecting a motion in the x, y and z-axis;
a second accelerometer for detecting a tilt about the z-axis;
at least one acoustic sensor for detecting sound related to the patient's breath;
a memory comprising a lookup table, a real-time clock, and one or more instructions; and
a processor, wherein the processor:
calculates motion values from signals received from the first accelerometer;
calculates tilt values from signals received from the second accelerometer;
calculates sound values from signals received from the acoustic sensor;
filters the motion values and the rotation values according to limitations stored in the lookup table, to provide filtered motion values;
filters the sound values according to limitations stored in the lookup table, to provide filtered sound values;
assigns a time stamp to each filtered motion value and each filtered sound value using the real-time clock within the memory;
determines local maximums for the filtered motion values and local minimums for the filtered sound values; and
counts and stores a completed breath for every time one of the local maximums for the filtered motion values occurs during one of the local minimums for the filtered sound values.

9. The method of claim 8, wherein the memory further comprises instructions that cause the processor to disregard the local minimums for the filtered sound values that do not match the local maximums for the filtered motion values.

10. The method of claim 8, wherein the memory further comprises instructions that cause the processor to count the completed breaths and calculate a respiration rate using assigned time stamps.

11. The method of claim 10, wherein the device further comprises a display screen, wherein the display screen displays the respiration rate.

12. The method of claim 10, wherein the memory further comprises instructions that cause the processor to wirelessly transfer the counted breath count to an external device.

13. The method of claim 8, wherein the device is attachable to a surface on the body.

14. The method of claim 8, wherein the device is disposable after a single use or a single patient.

15. A device for determining respiration in a patient, the device comprising:
a first accelerometer for detecting a motion in the x, y and z-axis;
a second accelerometer for detecting a tilt about the z-axis;
at least one acoustic sensor for detecting sound related to the patient's breath;
a memory comprising a lookup table, a real-time clock, and one or more instructions;
a processor configured to:
calculate motion values from signals received from the first accelerometer;
calculate tilt values from signals received from the second accelerometer;
calculate sound values from signals received from the acoustic sensor;
filters the motion values and the tilt values according to limitations stored in the lookup table, to provide filtered motion values;
filters the sound values according to limitations stored in the lookup table, to provide filtered sound values;
assigns a time stamp to each filtered motion value and each filtered sound value using the real-time clock within the memory;
determines local maximums for the filtered motion values and local minimums for the filtered sound values;
counts and stores a completed breath for every time one of the local maximums for the filtered motion values occurs during one of the local minimums for the filtered sound values;
calculates a respiration rate using the counted completed breaths and the assigned time stamps; and
a display screen, wherein the display screen displays the calculated respiration rate.

16. The device of claim 15, wherein the memory further comprises instructions that cause the processor to disregard the local minimums for the filtered sound values that do not match the local maximums for the filtered motion values.

17. The device of claim 15, wherein the device is attachable to a surface on the body.

18. The device of claim 15, wherein the memory further comprises instructions that cause the processor to wirelessly transfer the complete breath count to an external device.

19. The device of claim 15, wherein the device is disposable after a single use or a single patient.

* * * * *